United States Patent [19]

Ninomiya et al.

[11] Patent Number: 5,608,121
[45] Date of Patent: Mar. 4, 1997

[54] PROCESS FOR PRODUCING POLYHYDRIC ALCOHOL

[75] Inventors: Teruyuki Ninomiya; Toshio Watanabe; Akira Mori; Takaki Ikebe; Atsushi Iwamoto, all of Kurashiki, Japan

[73] Assignee: Mitsubishi Gas Chemical Company, Inc., Tokyo, Japan

[21] Appl. No.: 533,513

[22] Filed: Sep. 25, 1995

[30] Foreign Application Priority Data

Oct. 20, 1994 [JP] Japan .................................. 6-255352

[51] Int. Cl.$^6$ .................................................. C07C 31/18
[52] U.S. Cl. ................................................................ 568/852
[58] Field of Search ............................................. 568/852

[56] References Cited

U.S. PATENT DOCUMENTS 4,642,391  2/1987  Rogier ..................................... 568/624

OTHER PUBLICATIONS

A. H. Blatt, 'Organic Syntheses', Collective Vol. 1, 2nd Edition, 1947, John Wiley & Sons, New York, NY, pp. 425–427.
H. F. Mark et al., 'Kirk–Othner Encyclopedia of Chemical Technology, 3rd. Edition', 1978, John Wiley & Sons, New York, pp. 778–779.

P. W. Sherwood, 'Here's the Complete Story on This Petrochemical . . . Pentaerythritol', Petroleum Refiner, vol. 35, No. 11, Nov. 1956, Houston, pp. 171–179.
B. Weibull et al, 'The Synthesis of Some 1,1,1–trishydroxy–methylalkanes', ACTA Chemica Scandinavica, vol. 16, No. 4, 1962, Amsterdam, NL, p. 1062.
C. Paal et al, 'Über die katalytische Spaltung und Oxydation der Amiensäure', Berichte der Deutschen Chemischen Gesellschaft, vol. 57, 1926, Weinheim DE, pp. 1511–1526.

Primary Examiner—Joseph Conrad
Attorney, Agent, or Firm—Frishauf, Holtz, Goodman, Langer & Chick, P.C.

[57] ABSTRACT

There is disclosed a process for producing a polyhydric alcohol which comprises reacting an aliphatic aldehyde with formaldehyde in the presence of a base compound consisting essentially of a hydrogencarbonate and a carbonate which have been formed by the oxidation or hydrolysis of a formic acid salt, in particular, the process according to the above process wherein a formic acid salt which has been by-produced by the reaction of an aliphatic aldehyde with formaldehyde is oxidized or hydrolyzed in the presence of a noble metal catalyst or a nickel catalyst in a reductive state to form a base compound consisting essentially of a hydrogencarbonate and a carbonate and this base compound is circulated through the reaction of the aldehyde and formaldehyde and is reused as the base compound. The above process enables easy and highly efficient production of high quality polyhydric alcohols substantially without by-producing a formic acid salt with a low value-added.

9 Claims, 1 Drawing Sheet

FIG. 1

PROCESS FOR PRODUCING POLYHYDRIC ALCOHOL

BACKGROUND OF THE INVENTION

1. Field of the invention

The present invention relates to a process for producing a polyhydric alcohol which is useful as a raw material for polyester resins, alkyd resins, polyurethane resins, polycarbonate resins, plasticizers, surfactants, lubricating oils, basis for cosmetics, reactive monomers and the like.

2. Description of the Related Arts

There is known, as a process for producing a polyhydric alcohol, a two-stage reaction process in which an aliphatic aldehyde and formaldehyde are subjected to an aldol condensation reaction, and subsequently to a crossed Cannizzaro reaction each in the presence of a base catalyst, said aliphatic aldehyde being represented by the formula (i)

(i)

wherein $R^1$, $R^2$ and $R^3$ are each a hydrogen atom or a straight-chain or branched aliphatic hydrocarbon group having 1 to 22 carbon atoms with the proviso that at least one of them is a hydrogen atom.

The above-mentioned process is described in Japanese Patent Application Laid-Open No. 139141/1988 corresponding to U.S. Pat. No. 4,814,509, Japanese Patent Application Laid-Open No. 162538/1983 corresponding to U.S. Pat. No. 4,514,578 end the like, but each process described therein is based on the premise that the objective polyhydric alcohol is produced in combination with a formic acid salt.

Examples of the base catalyst to be used in the above-mentioned process include a hydroxide of an alkali metal or an alkaline earth metal and a carbonate of any of the aforesaid metals, which are exemplified by sodium hydroxide, potassium hydroxide, calcium hydroxide, lithium hydroxide, sodium carbonate, potassium carbonate, calcium carbonate and lithium carbonate; and an amine compound, especially a tertially amine such as trimethylamine, triethylamine, diethylmethylamine, dimethylethylamine, diisopropylamine and tributylamine.

As a process for producing neopentyl glycol (hereinafter abbreviated to "NPG") which is one of polyhydric alcohols, there is described a process in which hydroxypivaldehyde (hereinafter abbreviated to "HPA") is synthesized at first by an aldol condensation reaction in the first reaction stage and then the resultant HPA is hydrogenated into NPG in Japanese Patent Application Publication No. 53421/1982 corresponding to EP 44412, Japanese Patent Application Laid-Open No. 299239/1989 corresponding to U.S. Pat. No. 4933493, and Japanese Patent Application Laid-Open No. 182442/1992 corresponding to U.S. Pat. No. 5,395,989, and the like patent.

A process for producing trimethylol propane (hereinafter abbreviated to "TMP") which comprises effecting hydrogenation after the aldol condensation reaction in the same manner as above is described in Japanese Patent Application Laid-Open No. 92705/1978 corresponding to U.S. Pat. No. 412,290, Japanese Patent Application Laid-Open No. 287738/1988 corresponding to U.S. Pat. No. 5,149,861 and the like.

The production of a polyhydric alcohol in the presence of a base catalyst is accompanied with the by-production of a formic acid salt in an equimolar amount to the polyhydric alcohol as the main objective product. The formic acid salt as the by-product is utilized, for example, for the production of a hydrosulfite, etc., but is limited in its demand. Thus it follows that most of the by-produced formic acid salt is inevitably subjected to waste disposal, which incurs great expense, since it is accompanied by environmental pollution.

On the other hand, the process for producing NPG which comprises an aldol condensation reaction and successive hydrogenation requires a high pressure of about 50 to 150 kg/cm² in the hydrogenation reaction, thereby complicating the production equipment.

Moreover in the case of producing TMP by a process similar to the above, the objective TMP is obtained only at a low yield and less production rate per unit time; besides there has never been found an example demonstrating an industrial production of TMP by the foregoing process.

SUMMARY OF THE INVENTION

As a result of intensive research and investigation made by the present inventors on a process for producing a polyhydric alcohol involving the above-mentioned problems or difficulties, it has been found that a polyhydric alcohol can effectively be produced by a method in which a formic acid salt which has been by-produced by a crossed Cannizzaro reaction is oxidized or hydrolyzed in the presence of a noble metal catalyst or a nickel catalyst in a reductive state to form a base compound composed essentially of a hydrogencarbonate; and the resultant base compound, as it is or after being heated or concentrated by heating to convert most of the hydrogencarbonate into a carbonate, is circulated through the reaction system so that the base compound functions as a catalyst to contribute to the effective production of a polyhydric alcohol. The present invention has been accomplished by the above-mentioned finding and information.

Specifically the present invention provides a process for producing a polyhydric alcohol which comprises reacting an aliphatic aldehyde with formaldehyde in the presence of a base compound comprising, as principal components, a hydrogencarbonate and a carbonate which have been formed by the oxidation or hydrolysis of a formic acid salt, said aliphatic aldehyde being represented by the general formula (i)

(i)

wherein $R^1$, $R^2$ and $R^3$ are each a hydrogen atom or a straight-chain or branched aliphatic hydrocarbon group having 1 to 22 carbon atoms with the proviso that at least one of them is a hydrogen atom.

The present invention also provides a process for producing a polyhydric alcohol according to the above-mentioned process wherein a formic acid salt which has been by-produced by the reaction of an aliphatic aldehyde with formaldehyde is oxidized or hydrolyzed in the presence of a noble metal catalyst or a nickel catalyst in a reductive state to form a base compound comprising, as principal components, a hydrogencarbonate and a carbonate and the resultant base compound is circulated and reused through the reaction system.

DESCRIPTION OF THE PREFERRED EMBODIMENTS

The reaction of an aliphatic aldehyde with formaldehyde for the purpose of producing a polyhydric alcohol according to the present invention is a two-stage reaction comprising an aldol condensation reaction and a crossed Cannizzaro reaction. A series of reactions including an aldol condensation reaction as the first step, a crossed Cannizzaro reaction, a reaction for producing a hydrogencarbonate from the by-produced formic acid salt and a reaction for converting the resultant hydrogencarbonate to a carbonate are represented by the following reaction formulae with reference to the production of TMP from n-butylaldehyde (hereinafter abbreviated to "NBAL") as a typical example of reaction according to the present invention.

(1) Aldol condensation reaction $$CH_3CH_2CH_2CHO+2HCHO \rightarrow CH_3CH_2C(CH_2OH)_2CHO$$

(2) Crossed Cannizzaro reaction $$CH_3CH_2C(CH_2OH)_2CHO+HCHO+Na_2CO_3+H_2O \rightarrow$$
$$CH_3CH_2C(CH_2OH)_3+HCOONa+NaHCO_3$$

(3) Reaction for producing hydrogencarbonate from formic acid salt (3-1) In the case of oxidation $$HCOONa+1/2O_2 \rightarrow NaHCO_3$$

(3-2) In the case of hydrolysis $$HCOONa+H_2O \rightarrow NaHCO_3+H_2$$

(4) Reaction for converting hydrogencarbonate to carbonate $$2NaHCO_3 \rightarrow Na_2CO_3+H_2O+CO_2$$

The resultant carbonate is circulated and reused through the reaction system, since it is not only a catalyst for the crossed Cannizzaro reaction, but also a reactive substance.

The aliphatic aldehyde represented by the general formula (i) according to the present invention may be either a synthetic product or a natural product, and is exemplified by acetaldehyde, propionaldehyde, n-butyraldehyde, isobutyraldehyde, pentanal, hexanal, heptanal, octanal, decanal, dodecanal, tetradecanal, hexadecanal, eicosanal, docosanal, octadecanal, isopalmitylaldehyde, isostearylaldehyde and isodocosanal. These aldehydes may be used alone or in combination with at least one other.

The formaldehyde to be used in the present invention may be in the form of aqueous solution or in the form of solid, that is, paraformaldehyde and is properly selected according to the type of the objective polyhydric alcohol to be produced.

The amount of the formaldehyde to be used varies in theoretical and practical molar amounts depending on the type of the objective polyhydric alcohol to be produced. For example, in the case of isobutyraldehyde (hereinafter abbreviated to "IBAL") wherein one of $R^1$, $R^2$ and $R^3$ is H and the other two are each —$CH_3$ in the general formula (i), the molar ratio of formaldehyde to IBAL is 2.0 to 2.5. In the case of NBAL wherein two of $R^1$, $R^2$ and $R^3$ are each H and the other one is —$C_2H_5$ in the general formula (i), the molar ratio of formaldehyde to IBAL is 3.0 to 6.0. Further in the case of an aliphatic aldehyde wherein two of $R^1$, $R^2$ and $R^3$ are each H and the other one is an aliphatic hydrocarbon group having 6 to 22 carbon atoms in the general formula (i), the molar ratio of formaldehyde to the aforesaid aliphatic aldehyde is 3.0 to 8.0.

The base compound to be present in the aldol condensation reaction and the crossed Cannizzaro reaction according to the present invention is a hydrogencarbonate to be formed by the oxidation or hydrolysis of a formic acid salt. However, since the hydrogencarbonate is partially turned into the corresponding carbonate at a temperature of 50° C. or higher while releasing $CO_2$ gas, the base compound is substantially a mixture of the hydrogencarbonate and the carbonate.

The formic acid salt or the hydrogencarbonate and carbonate may be any of sodium, potassium, lithium, calcium and ammonium salts, but in the case of industrial practice, a sodium salt is most general.

The amount of the base compound to be used is 1 to 5 times expressed in terms of the molar ratio of said compound to the aliphatic aldehyde. In order to produce the objective polyhydric alcohol in high yield by suppressing the formation of by-products, it is necessary to regulate the above-mentioned molar ratio in accordance with the type of the aliphatic aldehyde to be used. For example, suitable molar ratios are 2.01 to 2.10 for the aliphatic aldehyde being IBAL and 3 to 4 for an aliphatic aldehyde having 6 to 22 carbon atoms.

As described hereinbefore, in the crossed Cannizzaro reaction a formic acid salt is produced by the reaction of the base compound with the formic acid which is formed from an alkanal and formaldehyde. There is used, as a catalyst for the aldol condensation reaction and crossed Cannizzaro reaction in the present invention, the mixture of a hydrogencarbonate which is formed by the oxidation or hydrolysis of the above-mentioned formic acid salt and a carbonate formed from the aforesaid hydrogencarbonate. The reaction for producing the hydrogencarbonate and carbonate (hereinafter referred to as "basic conversion reaction") is put into practice in an aqueous solution in the presence of a noble metal catalyst such as Ru, Rh, Pd, Pt, Os and Ir or a nickel catalyst in a reductive state.

In the process according to the present invention, the aldol condensation reaction as the first stage reaction and the crossed Cannizzaro reaction as the second stage reaction may be carried out under respective reaction conditions independent of one another or in the same reactor without distinguishing from each other. Both the reactions are performed usually in the absence of a solvent in the case of a lower aliphatic aldehyde in which one or two of $R^1$ $R^2$ and $R^3$ are each an aliphatic hydrocarbon group having 1 to 4 carbon atoms in the general formula (i). On the other hand, in the case of an aliphatic aldehyde in which one or two of $R^1$, $R^2$ and $R^3$ are each an aliphatic hydrocarbon group having 5 to 22 carbon atoms, both the reactions are carried out in a reaction solvent consisting of a tertiary alcohol such as tert-butyl alcohol, tert-heptyl alcohol, etc. in an amount of preferably 0.5 to 10 times based on the aliphatic aldehyde of the general formula (i).

The temperature of the raction between the aliphatic aldehyde and formaldehyde is −5° to 110° C., preferably 25° to 60° C., and the optimum reaction temperature varies to some extent depending upon the type of the aliphatic aldehyde. For example in the case of producing trimethylol ethane (hereinafter abbreviated to "TME") from propionaldehyde in which two of $R^1$, $R^2$ and $R^3$ are each H and one of them is —$CH_3$ in the general formula (i), the reaction temperature is 30° to 80° C. In the case of producing trimethylol nonane from decanal, it is preferable that the reaction temperature be 25° to 60° C. and that the reactant be matured for about one hour at a reaction temperature of 60° C.

The base compound to be used in the present invention is a mixture of a hydrogencarbonate and a carbonate, and thus the crossed Cannizzaro reaction as the second stage reaction is accompanied by the generation of carbon dioxide gas.

It is therefore preferable to proceed with the reaction discontinuously or continuously at reduced pressure or atmospheric presure or under pressure, preferably under a pressure of 1 to 2.3 kg/cm² while discharging $CO_2$ gas outside the reaction system so as to prevent the evil of $CO_2$ bubbling, that is, prevent the gas-liquid mixture from spouting or overflowing from the reactor.

In view of the foregoing, in the case of producing TMP by the reaction of NBAL with formaldehyde there is adopted a method in which NBAL and a basic solution containing the mixed salt of the hydrogencarbonate and carbonate are each firstly added dropwise at a constant rate through individual nozzles in the aqueous solution of formaldehyde.

There are available several methods for producing the objective polyhydric alcohol from the reactants thus obtained, which methods however, vary depending upon the conditions under which the reaction has been carried out. Also the method for treating the reaction products varies depending upon the physical properties of the objective polyhydric alcohol, especially the difference in the solubility of the alcohol in water.

For example in the case of producing TMP, the reaction product is concentrated until the concentration of the formic acid salt in the reaction product reaches 25 to 30% by weight and thereafter, the objective TMP and the formic acid salt are separated from each other by means of solvent extraction. The solvent to be used for the extraction is selected from NBAL that is also a raw material for the reaction and effective species including a ketone such as methyl ethyl ketone and methyl isobutyl ketone, an alcohol such as isobutyl alcohol and isopropyl alcohol and an ester such as butyl acetate ester.

In the case of producing pentaerythritol (hereinafter abbreviated to "PE") from acetaldehyde in which all of $R^1$, $R^2$ and $R^3$ are each H in the general formula (i), the reaction products are concentrated followed by cooling, and the crystallized PE is subjected to solid-liquid separation from the formic acid salt in the aqueous solution. The PE separated as the cake is washed with water and dried into a finished product.

In the case of producing polyhydric alcohol from an aliphatic aldehyde in which two of $R^1$, $R^2$ and $R^3$ are H and the other has 5 to 22 carbon atoms in the general formula (i), for example, producing trimethylol heptane (hereinafter abbreviated to "TMH") from octanal having 8 carbon atoms, the objective TMH and the formic acid salt can be separated from each other by adding water to the reaction products to separate them into an organic phase and water phase. The TMH in the organic phase is separated from the solvent by distilling away the solvent and thereafter, further purified into a highly pure TMH.

On the other hand, the formic acid salt which has been separated into the water phase is transferred to a formic acid salt convertor, as it is or after being treated with an activated carbon for removing the substances responsible for the deterioration of the catalyst such as organic acid salts other than sodium formate, formaldehyde concentrates and formoses formed from formaldehyde, followed by regulation of the sodium formate concentration with water. There, the activated carbon-treated or nontreated salt is converted into a base compound comprising a hydrogencarbonate as a principal component in the presence of a noble metal catalyst or a nickel catalyst in a reductive state in the presence or absence of oxygen atoms, that is, generally air.

The activated carbon to be used may be of any type of coconut shell-based and coal-based types and may be of any shape of granule, activated carbon fiber, honeycomb, sheet and molded activated carbon.

Examples of the noble metal catalyst to be used for the basic conversion reaction which converts a formic acid salt into a hydrogencarbonate and a carbonate include Ru, Rh, Pd, Pt, Os, Ir, Au and Ag, among which Pd and Ru are particularly effective. The catalyst may be a multi-component catalyst containing at least two noble metals mixed with each other.

The above-mentioned nickel catalyst in a reductive state is a general reductive nickel catalyst to be used for hydrogenation reaction, etc. and is exemplified by developed Raney nickel, reductive nickel available on the market, stabilized nickel, nickel formate, etc.

The aforesaid catalysts may be supported on carbon or the oxide of Al, Zr, Ti or the like and also may be in the form of any of flake, sphere, cylinder and powder. The method of using the catalyst may be any of fixed bed system and suspension system.

The basic conversion reaction by which the formic acid salt is converted into the hydrogencarbonate, which is further converted into the carbonate through the oxidation or hydrolysis is put into practice by a conventional method at a temperature of 50° to 200° C., preferably 60° to 160° C. under atmospheric pressure to 100 kg/cm² pressure.

The resultant base compound containing the hydrogencarbonate and carbonate, as it is or after being concentrated by heating to convert the most of the hydrogencarbonate into the carbonate, is circulated through a reactor to be used for the aldol condensation reaction and the crossed Cannizzaro reaction.

DETAILED DESCRIPTION OF THE DRAWINGS

Figure 1:
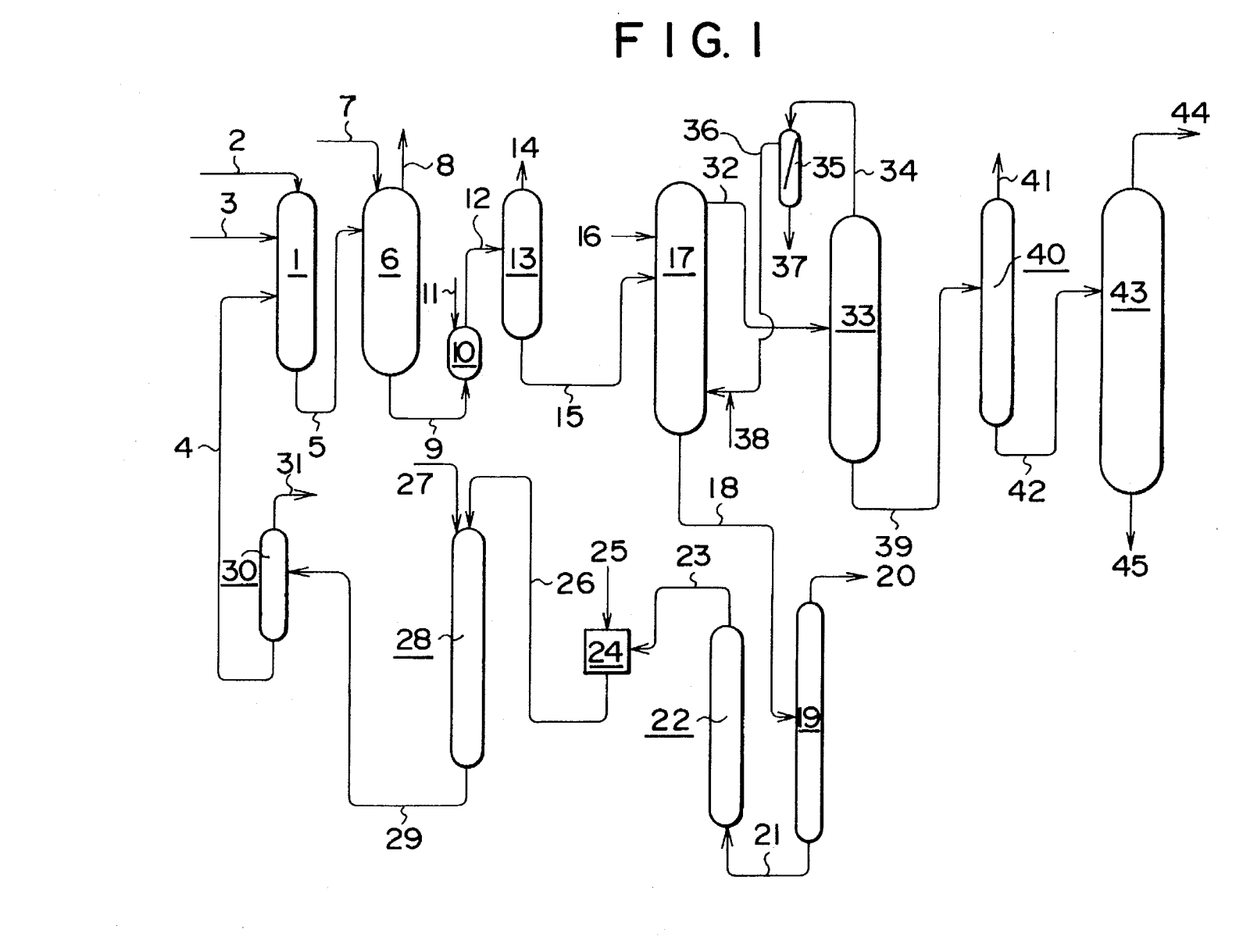
FIG. 1 is a schematic process flow diagram showing an example of equipment for producing a polyhydric alcohol according to the present invention.

The present invention will be illustrated with reference to the drawing. Drawing 1 is a schematic process flow diagram showing an example of equipment for producing a polyhydric alcohol according to the present invention, specifically, for producing TMP from NBAL. With reference to Drawing 1, to an aldol condensation reactor 1 are fed formaldehyde through line 2, NBAL through line 3 and mixed solution of sodium hydrogencarbonate and sodium carbonate which solution has been recovered in the post-step through line 4 to proceed with the aldol condensation reaction.

Next, the aldol condensation reaction liquid thus obtained is transferred to a crossed Cannizzaro reactor 6 through line 5 and sodium hydroxide is also fed to the reactor 6 through line 7 to proceed with the crossed Cannizzaro reaction.

Here, the quantity of the sodium hydroxide to be fed through line 7 is determined by the quantities of the sodium hydrogencarbonate and sodium carbonate that are converted from sodium formate and are recovered in the post-step. That is to say, when the recovery rate is 98%, it follows that the shortage of alkali quantity is 2%, thereby necessitating a supplement corresponding to the non-recovered rate.

Since in the process according to the present invention the base compound resulting from the crossed Cannizzaro reaction comprises sodium hydrogencarbonate and sodium carbonate as principal components, carbon dioxide ($CO_2$) gas is generated at the time of the reaction and thus the reaction is carried out while the generated $CO_2$ is purged outside through line 8.

The resultant crossed Cannizzaro reaction liquid is transferred to a neutralization vessel 10 through line 9 and is neutralized with formic acid which is fed through line 11 to pH 7.0. The neutralized reaction liquid is transferred through line 12 to a concentration column 13, where the liquid is concentrated so that the concentration of the sodium formate reaches 25 to 30% by weight, while water is distilled away outside the system through line 14.

To an extraction column 17 are fed the concentrated reaction liquid at the middle stage thereof through line 15, an extraction solvent at the lower part of the middle stage thereof through lines 36 and 38, and washing water at the upper part of the middle stage thereof through line 16 to continuously proceed with solvent extraction. The extract and raffinate are each withdrawn through line 32 at the upper stage of the column 17 and through line 18 at the lower stage thereof, respectively.

The raffinate thus withdrawn is transferred to a distillation column for treating raffinate 19, where the low boiling fractions such as the slightly remaining solvent, etc. are distilled away through line 20, while the residue in the column bottom is transferred through line 21 to an activated carbon treatment column 22, where the substances causing the deterioration of the catalyst are removed. The residue thus treated is transferred through line 23 to a dilution vessel 24, where the sodium formate is regulated to a concentration of 12 to 18% by weight by the water supplied through line 25.

The solution of sodium formate thus regulated is transferred through line 26 to a formic acid salt convertor 28, where the sodium formate is converted into sodium hydrogencarbonate in the presence of a noble metal catalyst or a nickel catalyst in a reductive state, while air is supplied through line 25 according to the demand. In the case where the conversion temperature is 50° C. or higher, a part of sodium hydrogencarbonate is converted into sodium carbonate and the resultant convertion liquid may be fed to the aldol condensation reactor 1. In order to further enhance the basicity of the convertion liquid, it customary that the conversion liquid which is discharged from the formic acid salt convertor 28 be transferred through line 29 to a heating vessel 30, where most of the sodium hydrogencarbonate is converted into sodium carbonate by being heated to 90° to 100° C., while the carbon dioxide gas generated during the conversion is released outside the system through line 31.

The liquid resulting from the conversion of sodium formate into sodium hydrogencarbonate and further into sodium carbonate is fed through line 4 to aldol condensation reactor 1 for use in the successive reaction.

On the other hand, the extract liquid which is taken out from the extraction column 17 at the upper stage is transferred through line 32 to an extract stripper 33. The solvent and dissolved water are distilled away from the stripper 33 through line 34 and transferred to a separation vessel 35, where they are seperated into a water phase and an organic phase. The water phase is taken out outside the system through line 37, while the organic phase is withdrawn through line 36 for reuse as the solvent.

The residue in the extract stripper 33 is transferred through line 39 to an initial distillation column 40, where low boiling components whose boiling points are lower than that of TMP are distilled away at the overhead through line 41 and crude TMP is taken out at the bottom. The crude TMP thus taken out is transferred through line 42 to a rectifying column 43 and purified to afford purified TMP through line 44 connecting to the top of the column 43, while the residue is taken out therefrom through line 45 connecting to the bottom thereof.

According to the process of the present invention, it is made possible to efficiently and easily produce polyhydric alcohols substantially without by-producing a formic acid salt with a low value-added.

Specifically the process of the present invention prevents the discharge of a formic acid salt outside the process system except for the required amount thereof as a finished product and thereby solves the problem of unbalance in demand between polyhydric alcohols and formic acid salts.

Furthermore, the process of the present invention enables easy and highly efficient production of high quality polyhydric alcohols from an aliphatic aldehyde and formaldehyde, thus rendering itself highly advantageous from the industrial viewpoint.

In the following, the present invention will be described in more detail with reference to working examples, which however shall not be construed to limit the invention thereto.

EXAMPLE 1

[Production of trimethylol propane (TMP) from n-butyraldehyde (NBAL) and formaldehyde by using a noble metal catalyst in basic conversion reaction]

(First-stage reaction)

A basic aqueous solution containing 316.7 g (3.77 mol) of sodium hydrogencarbonate and 20.1 g (0.19 mol) of sodium carbonate, and 289 g (4.0 mol) of NBAL were added each through an independent nozzle in 3200 g (12.78 mol) of 12% by weight aqueous Solution of formaldehyde over a period of 0.5 hour so as not to directly mix NBAL with the basic aqueous solution, while the reaction was continued for 30 minutes at a reaction temperature maintained at 30° to 75° C. Immediately after the completion of the reaction, formic acid was added to the reaction system to neutralize the system to pH 7. Thereafter, the resultant reaction liquid was concentrated under reduced pressure until the concentration of the sodium formate reached 20% by weight, and the concentrated reaction liquid was extracted three times separately by the use of 1500 g of NBAL as the solvent. The resultant three extraction liquids were mixed together, and the mixture was subjected to vacuum distillation to recover NBAL and subsequently to vacuum distillation at a vacuum of 1 mm Hg by the use of a Oldshue distillation column equipped with five distillation plates. As a result, after the removal of 43 g of the initial fraction, 479.7 g of TMP was obtained as the principal fraction, which corresponded to a yield of 89.5 mol % based on NBAL.

On the other hand, 772.5 g of the raffinate formed by NBAL extraction was allowed to pass through a glass tube with 13 mm inside diameter packed inside with 150 mL (milliliter) of activated carbon (produced by Kuraray Chemical Co., Ltd. under the trademark "Kuraraycoal GCL") at 50° C. at 0.2 hr$^{-1}$ LSV [liquid space velocity; flow rate of the fed raw material (mL/hr)/volume of the packed acitivated carbon (mL)]. Then, the raffinate thus treated was incorporated with 2049.5 g of water to regulate the concentration of the sodium formate to 10% by weight.

The aqueous solution of sodium formate as the raw liquid material was introduced in a packed-bed type tubular reactor with 15 mm inside diameter and 300 mm length equipped with a raw material feed pipe, an oxygen feed pipe, a heater as an external heat source and a cooling jacket to carry out a basic conversion reaction. The tubes uniformly packed inside with 0.5% by weight of Pd catalyst supported on carbon in a volume of 100 mL (milliliter) were charged at the top with the above-mentioned raw liquid material at 3.0 hr$^{-1}$ LSV [liquid space velocity: flow rate of the fed raw material (mL/hr)/volume of packed catalyst (mL)], while the internal oxygen partial pressure was automatically regulated to 3.5 kg/cm$^2$ by supplying air and the reaction temperature was automatically controlled to 130° C. with the heater as an external heat source and cooling water.

The compositional analysis result of the basic conversion liquid thus obtained is given in Table 3. It follows therefrom that the yield of the basic conversion liquid is 99 mol % expressed in terms of the ratio of the total amount of the sodium hydrogencarbonate and sodium carbonate to the feed amount of the sodium formate.

(Second-stage reaction)

The basic conversion liquid in a total amount of 2720.5 g which had been obtained in the preceding first-stage reaction and 289 g (4.0 mol) of NBAL were added in 852.9 g (12.78 mol) of 45% by weight of aqueous solution of formaldehyde over a period of 0.9 hour. Subsequently the reaction was put into practice in the same manner as in the first-stage reaction.

After the completion of the reaction, TMP was obtained by distillation in a yield of 91.0 mol % based on NBAL. The quality of TMP thus obtained together with that obtained in the first-stage reaction are given in Table 1.

In the same manner as in the first-stage reaction, the raffinate formed by NBAL extraction was made into an activated carbon-treated aqueous solution of sodium formate and converted into a basic conversion liquid comprising sodium hydrogencarbonate and sodium carbonate as principal components at a yield of the basic conversion liquid of 99.5 mol %.

(Third to tenth stage reaction)

The procedure in the second-stage reaction was repeated 8 times in total. As a result, the average yield of the basic conversion liquid in the third to tenth reaction was 99.6 mol %. The quality evaluation results of TMP in each stage of the reaction in Example 1 are given in Table 1.

TABLE 1

|  | First-stage reaction | Second-stage reaction | Third-stage reaction | Fourth-stage reaction | Fifth-stage reaction |
| --- | --- | --- | --- | --- | --- |
| Melting point (°C.) | 58.6 | 58.8 | 58.5 | 58.6 | 58.6 |
| Acid content | ≦0.001 | ≦0.001 | 0.001 | ≦0.001 | ≦0.001 |
| Water content | 0.02 | 0.02 | 0.03 | 0.02 | 0.03 |
| Ash content (%) | ≦0.001 | ≦0.001 | ≦0.001 | ≦0.001 | ≦0.001 |
| Melt color (APHA) | 20 | 15 | 20 | 10 | 10 |

|  | Sixth-stage reaction | Seventh-stage reaction | Eighth-stage reaction | Ninth-stage reaction | Tenth-stage reaction |
| --- | --- | --- | --- | --- | --- |
| Melting point (°C.) | 58.7 | 58.9 | 58.8 | 58.7 | 58.7 |
| Acid content | 0.001 | 0.001 | 0.001 | ≦0.001 | ≦0.001 |
| Water content | 0.03 | 0.03 | 0.02 | 0.01 | 0.03 |
| Ash content (%) | ≦0.001 | ≦0.001 | ≦0.001 | ≦0.001 | ≦0.001 |
| Melt color (APHA) | 15 | 10 | 10 | 15 | 10 |

EXAMPLE 2

[Production of pentaerythritol (PE) from acetaldehyde and formaldehyde by using a noble metal catalyst in basic conversion reaction]

(First-stage reaction)

A basic aqueous solution containing 269.09 g (3.2 mol) of powdery sodium hydrogencarbonate and 32 g (0.30 mol) of sodium carbonate, and 137.5 g (3.12 mol) of acetaldehyde were added each through an independent nozzle in 4500 g (29.97 mol) of 20% by weight aqueous solution of formaldehyde over a period of 0.8 hour so as not to directly mix acetal dehyde with the basic aqueous solution, while the reaction was continued for this period at a reaction temperature raised to 65° C. under regulating. The reaction was further continued for 40 minutes at a temperature maintained at 65° C. Immediately after the completion of the reaction, formic acid was added to the reaction system to neutralize the system to pH 7. Subsequently the formaldehyde remaining in the reaction liquid was recovered by distillation under pressure of 1.5 kg/cm² and thereafter, the remaining reaction liquid was concentrated under reduced pressure until the concentration of the sodium formate reached 15% by weight, the concentrated reaction liquid was cooled to 25° C. to crystallize PE, and the crystallized PE was recovered by separation with a contrifugal separator. Thus, finished product was obtained by drying in a yield of 356.4 g, which was equivalent to a yield of 84.0 mol % based on acetaldehyde.

On the other hand, the filtrate resulting from the primary centrifugal separation and the filtrate from washing with water in an amount of 1208 g was incorporated with 954 g of water end was subjected to basic conversion reaction in the same manner as in Example 1. As a result, the basic conversion liquid was obtained in a yield of 99.2 mol %. The compositional analysis result of the basic conversion liquid is given in Table 3.

(Second-stage reaction)

The basic conversion liquid in a total amount of 2620 g which had been obtained in the preceding first-stage reaction and 137.5 g (3.12 mol) of acetaldehyde were added each through an independent nozzle in 1995.3 g (29.97 mol) of 45% by weight of aqueous solution of formaldehyde over a period of 0.8 hour. Subsequently the reaction was put into practice in the same manner as in the first-stage reaction.

After the completion of the reaction, PE was obtained by crystallization in a yield of 84.5 mol % based on acetaldehyde. The quality of PE thus obtained together with that obtained in the first-stage reaction are given in Table 2.

In the same manner as in the first-stage reaction, the filtrate separated by centrifugal separation was subjected to a basic conversion reaction. As a result, the yield of the basic conversion product was 99.9 mol %.

TABLE 2

PE quality (Example 2)

|  | First-stage reaction | Second-stage reaction |
| --- | --- | --- |
| Melting point (°C.) | 183.1 | 183.0 |
| Monopentaerythritol (%) | 96.5 | 96.6 |
| Water content (%) | 0.06 | 0.07 |
| Ash content (%) | 0.06 | 0.06 |

TABLE 3

Compositional analysis of basic conversion liquid (% by weight)

|  | Example 1 | Example 2 |
| --- | --- | --- |
| Sodium formate | 0.83 | 0.80 |
| Sodium hydrongencarbonate | 10.74 | 6.53 |
| Sodium carbonate | 1.39 | 1.33 |
| Formaldehyde | 0.31 | 1.10 |
| Trimethylol propane | 0.04 | — |
| n-Butyraldehyde | 0.01 | — |
| Monopentaerythritol | — | 0.31 |
| Water | 85.96 | 88.98 |
| Others | 0.72 | 0.95 |

EXAMPLE 3

[Production of trimethylol nonane (TMN) from decanal end pareformaldehyde by using a noble metal catalyst in basic conversion reaction]

(First-stage reaction)

77.4 g (2.5 mol) of 97% by weight paraformaldehyde, 260 g of tert-heptyl alcohol, 71.5 g (0.85 mol) of sodium hydrogencarbonate and 8.0 g (0.07 mol) of sodium carbonate were blended. The resultant blend was maintained at 40° C. under stirring and subsequently incorporated with 80.0 g (0.51 mol) of decanal over a period of 4.0 hour, and further the reaction was continued for 1.0 hour, during which time the reaction temperature was finally raised to 87° C. Immediately after the completion of the reaction, formic acid was added to the reaction system to neutralize the system to pH 7. Thereafter, the resultant reaction liquid was incorporated with 120 g of water with stirring for 0.5 hour and then was allowed to stand. The liquid was separated into two phases. The organic phase was washed with water repeatedly, and the solvent was distilled away to afford 89.5 g of TMN as the reaction product, which was equivalent to a yield of 80.5 mol % based on decanal as a raw material. On the other hand, 495 g of the water phase separated from the organic phase was incorporated with 72 g of water and subjected to basic conversion reaction in the same manner as in Example 1. The reaction product thus obtained was concentrated to bone dryness at 90° C. or lower under reduced pressure. The yield of the basic conversion product was 95 mol %.

(Second-stage reaction)

By the use of the basic salt consisting essentially of sodium carbonate which was obtained by concentration to bone dryness, the second-stage reaction was performed in the same manner as the first-stage reaction. As a result of the reaction, TMN was obtained by two-phase separation in a yield of 81 mol % based on decanal. The yield of the basic conversion product was 96 mol %.

EXAMPLE 4

[Production of neopentyl glycol (NPG) from isobutyraldehyde (IBAL) and formaldehyde by using a noble metal catalyst in basic conversion reaction]

(First-stage reaction)

To 1126.1 g (15.0 mol) of 40% by weight formaldehyde maintained at 30° C. were added with stirring 514.9 g (7.14 mol) of IBAL and 667 g (8.0 mol) of 48% by weight sodium hydroxide over a period of 0.75 hour. The resultant mixture was heated to 60° C. and further to 65° C., and the reaction was continued for 10 minutes at 65° C. Immediately after the completion of the reaction, formic acid was added to the reaction system to neutralize the system to pH 7. The reaction product was extracted by the use of methyl isobutyl ketone (hereinafter abbreviated to "MIBK") as the solvent. The resultant extract was firstly subjected to vacuum distillation to recover MIBK and then was distilled under a reduced pressure of 70 mm Hg to afford 720.3 g of NPG, which was equivalent to a yield of 96.8 mol % based on IBAL.

On the other hand, low boiling components such as methanol that were contained in the raffinate were distilled away. In addition, the formaldehyde remaining in a concentration of about 1% in the raffinate was recovered in the form of hydroxypivaldehyde ("HPA") as a precursor of NPG by means of an aldol condensation reaction with IBAL in the presence of sodium hydroxide as the catalyst. In more detail, the aldol condensation reaction product was allowed to stand and separated into two phases. The upper phase, that is, IBAL phase containing HPA was used as the starting material IBAL for the next time, while the raffinate in the lower phase was diluted with water so that the sodium formate was diluted to a concentration of 11% by weight and then was subjected to basic conversion reaction in the same manner as in Example 1. As a result, the basic converision product was obtained in a yield of 100 mol %.

(Second-stage reaction)

The basic conversion liquid in a total amount which had been obtained in the preceding first-stage reaction and 514.9 g (7.14 mol) of IBAL containing the aforestated HPA were added in 790.3 g (15.0 mol) of 57% by weight of aqueous solution of formaldehyde over a period of 0.75 hour. Subsequently the reaction was put into practice in the same manner as in the first-stage reaction.

After the completion of the reaction, NPG was obtained by extraction and distillation in a yield of 96.0 mol % based on IBAL. On the other hand, the yield of the basic conversion product was 99.9 mol %.

EXAMPLE 5

[Production of trimethylol propane (TMP) from n-butyraldehyde (NBAL) and formaldehyde by using a nickel catalyst in a reductive state in basic conversion reaction]

(First-stage reaction)

A basic aqueous solution containing 95.4 g (0.90 mol) of sodium carbonate and 54.6 g (0.75 mol) of NBAL were added each through an independent nozzle in 485 g (2.42 mol) of 15% by weight aqueous solution of formaldehyde over a period of 0.5 hour, while the reaction temperature was raised from 30° to 90° C., and further the reation was continued for 30 minutes at 90° C. Immediately after the completion of the reaction, formic acid was added to the reaction system to neutralize the system to pH 7. Thereafter, the resultant reaction liquid was concentrated under reduced pressure until the concentration of the sodium formate reached 25% by weight, and the concentrated reaction liquid was extracted three times separately by the use of 600 g of NBAL as the solvent. The resultant three extraction liquids were mixed together, and the mixture was subjected to atmospheric distillation to recover NBAL and dissolved water and subsequently to vaccum distillation at a vacuum of 1 mm Hg by the use of a Oldshue distillation column equipped with five distillation plates. As a result, after the removal of 3.8 g of the initial fraction, 75.2 g of TMP was obtained as the principal fraction, which corresponded to a yield of 75.0 mol % based on NBAL.

On the other hand, 151.0 g of the raffinate formed by NBAL extraction was allowed to pass through a glass tube with 13 mm inside diameter packed inside with 150 mL (milliliter) of activated carbon (produced by Kuraray Chemicl Co., Ltd. under the trademark "Kuraraycoal GCL") at 50° C. at 0.2 hr$^{-1}$ LSV [liquid space velocity; flow rate of the fed raw material (mL/hr)/volume of the packed activated carbon (mL)]. Then, the raffinate thus treated was incorporated with 320.0 g of water to regulate the concentration of the sodium formate to 13% by weight.

The Raney nickel to be used in the decomposition reaction of sodium formate was prepared in the following procedure. To 400 g of 20% aqueous solution of sodium hydroxide contained in a 1000 mL (milliliter) beaker was gradually added 75 g of Raney nickel alloy containing 50% by weight of nickel and 50% by weight of aluminum, while the system was maintained at a temperature of 30° C. or lower. After all the Raney nickel alloy was added, the system was heated to 110° C., after 4 hours was incorporated with 100 mL of 20% by weight aqueous solution of sodium hydroxide, and was further heated for 3 hours. After hydrogen generation was finished, the system was allowed to cool to room temperature and washed with water rapeatedly to carry out development procedure until the washing water was brought to about pH 8.

In a 500 mL autoclave made of SUS and equipped with a stirrer were placed 470 g of 13% by weight aqueous solution of sodium formate as prepared by the TMP synthesis reaction and 30 g of the developed Raney nickel as prepared in the above-mentioned procedure with stirring at 180° C., while the system pressure was regulated to 15 kg/cm$^2$ with air. After 5 hours, the system was allowed to cool to room temperature, and the catalyst was filtered off to afford a basic conversion liquid. As a result of compositional analysis of the decomposed liquid, the yield of the basic conversion product was 81.9 mol % of the theoretical value.

(Second-stage reaction)

The basic conversion liquid in a total amount of 470.0 g which had been obtained in the preceding first-stage reaction and 44.3 g (0.61 mol) of NBAL were added in 181.7 g (2.42 mol) of 40% by weight of aqueous solution of formaldehyde over a period of 0.9 hour. Subsequently the reaction was put into practice in the same manner as in the first-stage reaction.

After the completion of the reaction, TMP was obtained by distillation in a yield of 75.5 mol % based on NBAL. The quality of TMP thus obtained together with that obtained in the first-stage reaction are given in Table 4.

In the same manner as in the first-stage reaction, the raffinate formed by NBAL extraction was made into an activated carbon-treated aqueous solution of sodium formate and converted into a basic conversion liquid comprising sodium hydrogencarbonate and sodium carbonate as principal components at a yield of the basic conversion product of 80.8 mol %.

TABLE 4

| TMP quality (Example 5) | | |
|---|---|---|
| | First-stage reaction | Second-stage reaction |
| Melting point (°C.) | 59.5 | 58.9 |
| Acid content (%) | ≦0.001 | ≦0.001 |
| Water content (%) | 0.02 | 0.02 |
| Ash content (%) | ≦0.001 | ≦0.001 |
| Melt color (APHA) | 20 | 10 |

EXAMPLE 6

[Production of pentaerythritol (PE) from acetaldehyde end formaldehyde by using a nickel catalyst in a reductive state in basic conversion reaction]

(First stage-reaction)

A basic aqueous solution containing 142.8 g (1.7 mol) of sodium hydrogencarbonate and 32 g (0.30 mol) of sodium carbonate, and 89.3 g (2.03 mol) of acetaldehyde were added each through an independent nozzle in 1680 g (11.19 mol) of 20% by weight aqueous solution of formaldehyde over a period of 0.8 hour so as not to directly mix acetaldehyde with the basic aqueous solution, while the reaction was continued for this period at a reaction temperature raised to 85° C. under regulating. The reaction was further continued for 40 minutes at a temperature maintained at 85° C. Immediately after the completion of the reaction, formic acid was added to the reaction system to neutralize the system to pH 7. Subsequently the formaldehyde remaining in the reaction liquid was recovered by distillation under pressure of 1.5 kg/cm$^2$ and thereafter, the remaining reaction liquid was concentrated under reduced pressure until the concentration of the sodium formate reached 25% by weight, the concentrated reaction liquied was cooled to 25° C. to crystallize PE, and the crystallized PE was recovered by separation with a centrifugal separator. Thus, finished product was obtained by drying in a yield of 231.9 g, which was equivalent to a yield of 84.0 mol % based on acetaldehyde.

On the other hand, the filtrate resulting from the primary centrifugal separation and the filtrate from washing with water in an amount of 760 g was incorporated with 420 g of water, was treated with the activated carbon, and was subjected to basic conversion reaction in the same manner as in Example 5. As a result, the basic conversion liquid was obtained in a yield of 90.6 mol %.

(Second-stage reaction)

The basic conversion liquid in a total amount of 1180 g which had been obtained in the preceding first-stage reaction and 189.3 g (2.03 mol) of acetaldehyde were added in 840.4 g (11.19 mol) of 40% by weight of aqueous solution of formaldehyde over a period of 0.8 hour. Subsequently the reaction was put into practice in the same manner as in the first-stage reaction.

After the completion of the reaction, PE was obtained by crystallization in a yield of 84.5 mol % based on acetaldehyde. The quality of PE thus obtained together with that obtained in the first-stage reaction are given in Table 5.

In the same manner as in the first-stage reaction, the filtrate separated by centrifugal separation was subjected to a basic conversion reaction. As a result, the yield of the basic conversion product was 99.7 mol %.

TABLE 5

| PE quality (Example 6) | | |
|---|---|---|
| | First-stage reaction | Second-stage reaction |
| Melting point (°C.) | 183.2 | 183.1 |
| Monopentaerythritol (%) | 96.4 | 96.6 |
| Water content (%) | 05 | 0.07 |
| Ash content (%) | 0.02 | 0.05 |

EXAMPLE 7

[Production of neopentyl glycol (NPG) from isobutyraldehyde (IBAL) and formaldehyde by using a nickel catalyst in a reductive state in basic conversion reaction]

(First-stage reaction)

To 1126.1 g (15.0 mol) of 40% by weight formaldehyde maintained at 30° C. were added with stirring 514.9 g (7.14 mol) of IBAL and 667 g (8.0 mol) of 48% by weight sodium hydroxide over a period of 0.75 hour. The resultant mixture was heated to 60° C. and further to 65° C., under regulating, and the reaction was continued for 10 minutes at 65° C. Immediately after the completion of the reaction, formic acid was added to the reaction system to neutralize the system to pH 7. The reaction product was extracted by the use of methyl isobutyl ketone (MIBK) as the solvent. The resultant extract was firstly subjected to vacuum distillation to recover MIBK and then was distilled under a reduced pressure of 70 mm Hg to afford 720.3 g of NPG, which was equivalent to a yield of 96.8 mol % based on IBAL.

On the other hand, low boiling components such as methanol that were contained in the raffinate were distilled away. In addition, the formaldehyde remaining in a concentration of about 1% in the raffinate was recovered in the form of hydroxypivaldehyde (HPA) as a precursor of NPG by means of an aldol condensation reaction with IBAL in the presence of sodium hydroxide as the catalyst. In more detail, the aldol condensation reaction product was allowed to stand and separated into two phases. The upper phase, that is, IBAL phase containing HPA was used as the starting material IBAL for the next time, while the raffinate in the lower phase was diluted with water so that the sodium formate was diluted to a concentration of 11% by weight.

The aqueous solution of sodium formate thus regulated was subjected to a basic conversion reaction by the use of a packed-bed type tubular reactor with 40 mm inside diameter and 1000 mm length equipped with a raw material feed pipe, a heater as an external heat source and a cooling jacket. The tube uniformly packed inside with 1000 mL of stabilized nickel was charged at the top with the above-mentioned raw liquid material at 1.0 hr$^{-1}$ LSV [liquid space velocity: flow rate of the fed raw material (mL/hr)/volume of packed catalyst (mL)], while the reaction temperature was automatically controlled to 160° C. with the heater as an external heat source and cooling water, and the system inside pressure was regulated to 15 kg/cm$^2$ with air.

As a result of further basic conversion reactions repeated 5 times, the yield of the basic conversion product reached at least 99.0 mol % of the theoretical value.

(Second-stage reaction)

The basic conversion liquid in a total amount which had been obtained in the preceding first-stage reaction and 514.9 g (7.14 mol) of IBAL containing the above-mentioned HPA were added in 790.3 g (15.0 mol) of 57% by weight of aqueous solution of formaldehyde over a period of 0.75 hour. Subsequently the reaction was put into practice in the same manner as in the first-stage reaction.

After the completion of the reaction, NPG was obtained by extraction and distillation in a yield of 94.5 mol % based on IBAL. As a result of further basic conversion reactions repeated 5 times, the yield of the basic conversion product reached at least 99.0 mol % of the theoretical value.

What is claimed is:

1. A process for producing a polyhydric alcohol which comprises reacting an aliphatic aldehyde with formaldehyde in the presence of a base compound comprising, as principal components, a hydrogencarbonate and a carbonate which have been formed by the oxidation or hydrolysis of a formic acid salt, said aliphatic aldehyde being represented by the general formula (i)

wherein $R^1$, $R^2$ and $R^3$ are each a hydrogen atom or a straight-chain or blanched aliphatic hydrocarbon group having 1 to 22 carbon atoms with the proviso that at least one of them is a hydrogen atom.

2. The process for producing a polyhydric alcohol according to claim 1 wherein a formic acid salt which has been by-produced by the reaction of an aliphatic aldehyde with formaldehyde is oxidized or hydrolyzed in the presence of a noble metal catalyst or a nickel catalyst in a reductive state to form a base compound comprising, as principal components, a hydrogencarbonate and a carbonate and the resultant base compound is circulated through the reaction of said aliphatic aldehyde and formaldehyde and is reused as said base compound as set forth in claim 1.

3. The process for producing a polyhydric alcohol according to claim 2 wherein the production of said base compound comprising a hydrogencarbonate and a carbonate by the oxidation or hydrolysis of a formic acid salt in the presence of a noble metal catalyst or a nickel catalyst in a reductive state, said formic acid being by-produced by the reaction of an aliphatic aldehyde with formaldehyde, is preceded by the previous treatment of said formic acid salt in the form of aqueous solution by the use of an activated carbon.

4. The process according to claim 2 wherein said noble metal catalyst is selected from the group consisting of palladium catalyst and ruthenium catalyst.

5. The process for producing a polyhydric alcohol according to claim 1 or 2 wherein said aliphatic aldehyde is at least one member selected from the group consisting of acetaldehyde, propionaldehyde, n-butyraldehyde, isobutyraldehyde, octanal and decanal.

6. The process according to claim 1 or 2 wherein said formic acid salt is sodium formate.

7. The process according to claim 1 or 2 wherein the amount of said base compound to be used is 1 to 5 times expressed in terms of the molar ratio of said base compound to the aliphatic aldehyde.

8. The process for producing a polyhydric alcohol according to claim 1 or 2 wherein said polyhydric alcohol is selected from the group consisting of trimethylol ethane (TME), trimethylol propane (TMP), penthaerythritol (PE), trimethylol nonane (TMN), neopentyl glycol (NPG) and trimethylol heptane (TMH).

9. The process according to claim 1 or 2 wherein the temperature of the reaction between the aliphatic aldehyde and formaldehyde is in the range of −5° to 110° C.

* * * * *